United States Patent [19]
Ishibashi

[11] Patent Number: 5,320,607
[45] Date of Patent: Jun. 14, 1994

[54] SIMPLE BLOOD SAMPLING DEVICE

[75] Inventor: Hiromu Ishibashi, Yokohama, Japan

[73] Assignee: Kabushiki Kaisya Advance, Tokyo, Japan

[21] Appl. No.: 3,054

[22] Filed: Jan. 11, 1993

[30] Foreign Application Priority Data

Feb. 13, 1992 [JP] Japan .............................. 4-013663[U]

[51] Int. Cl.⁵ .......................................... A61B 17/32
[52] U.S. Cl. ...................................... 604/115; 604/22
[58] Field of Search ....................... 604/22, 36, 48, 51, 604/73, 76, 115, 118, 181

[56] References Cited

U.S. PATENT DOCUMENTS

| | | | |
|---|---|---|---|
| 1,934,246 | 11/1933 | Demarchi | 604/115 |
| 2,660,169 | 11/1953 | Malm | 604/115 X |
| 3,626,929 | 12/1971 | Sanz et al. | 604/22 X |
| 4,299,219 | 11/1981 | Norris, Jr. | 604/115 |
| 4,395,870 | 7/1983 | Wagner | 604/115 |
| 4,518,387 | 5/1985 | Murphy et al. | 604/115 X |
| 5,037,431 | 8/1991 | Summers et al. | 604/22 X |
| 5,054,499 | 10/1991 | Swierczek | . |

FOREIGN PATENT DOCUMENTS 199484 10/1986 European Pat. Off. .
3708031 11/1987 Fed. Rep. of Germany .

OTHER PUBLICATIONS

J. Kimura et al., "Development in Method of Percutaneous Determination Blood Glucose Concentration with Ion Sensitive Field Effect Transistor Type Biosensor", BIO Industry, vol. 8, No. 11, pp. 30–38, published Nov. 1, 1991. Sampling of Exsudate by percutaneous suction is discussed at p. 31, rt. col., line 15 p. 32, lft. col., line 5, and FIGS. 1, 9 and 10.

English Summary of J. Kimura et al., Bio Industry, vol. 8, No. 11, pp. 30–38 (1991) published Nov. 1, 1991, "Development in Method of Percutaneous Determination of Blood Glucose Concentration . . . ".

Primary Examiner—Robert A. Hafer
Assistant Examiner—Sam Rimell
Attorney, Agent, or Firm—Wegner, Canton, Mueller & Player

[57] ABSTRACT

A simple blood sampling device composed of a vacuum chamber, a skin suction portion and a piercing and cutting means.

6 Claims, 4 Drawing Sheets

SIMPLE BLOOD SAMPLING DEVICE

BACKGROUND OF THE INVENTION

1. Field of the Invention

The present invention relates to a simple blood sampling device.

2. Description of the Related Art

In recent years, the numbers of persons suffering from various diseases derived from rich dietary patterns and increased stress, for example, diabetes, have been soaring. Trips to the hospital pose a major inconvenience to patients in their daily activity, so as examinations of blood sugar etc. over the course of the regular day become part of the daily routine, the method of sampling blood has come under attention as a large problem. The problem of the pain involved in the blood sampling becomes an even greater problem when it has to be repeated. In particular, this is becoming a further serious problem in the case of insulin-dependent patients, many of whom are small children. Further, in recent years, diseases transmitted through the blood have become social issues. To prevent AIDS, hepatitus, and other especially serious diseases, some sort of device which enables patients themselves to sample their own blood without problem is needed. However, no device has yet been proposed which enables blood to be sampled painlessly and simply.

SUMMARY OF THE INVENTION

Accordingly, the objects of the present invention are to eliminate the above-mentioned disadvantages in the prior art and to provide a device capable of sampling blood in a painless state.

Other objects and advantages of the present invention will be apparent from the following description.

In accordance with the present invention, there is provided a simple blood sampling device comprising a vacuum chamber, a skin suction portion, and a piercing and cutting means.

The present device is extremely simple in construction and further is small in size and light in weight and also does not use any special parts, so that the present device is low in price and can be used as a disposable device.

BRIEF DESCRIPTION OF THE DRAWINGS

The present invention will be better understood from the description set forth below with reference to the accompanying drawings; wherein.

DESCRIPTION OF THE PREFERRED EMBODIMENTS

The characteristics of the present device will now be explained.

A vacuum suction action is applied to a local portion of the surface of the skin of the subject (i.e., the living body). Along with this local vacuum suction, the area inside the subject's skin becomes engorged with blood and therefore the epidermis expands and rises up. This raised portion of the skin comes in contact with a piercing means provided at a predetermined position. Since the raised portion of the skin is sufficiently taut in state, the piercing means pierces the skin (epidermis) easily. When the piercing means pierces the skin, the blood engorged inside it flows out and is collected. Since the skin is locally drawn up, even though the piercing means pierces the skin, it does so instantaneously and the sensation of this is cancelled out by the stimulus caused by the suction action, so no pain is felt. Further, the piercing and cutting means pierce and cut in an engorged state, so the blood can be collected painlessly and reliably.

The vacuum chamber shown in the present device is a means for drawing up the surface of the subject's skin. Ones which perform the vacuum action mechanically and chemically may be mentioned. While not particularly limited to them, ampules, cassette devices, etc., which are formed in a vacuum state in advance by an air-tight material may also be mentioned. Further, the piercing and cutting means may be one or more solid needles, hollow needles, needles with sawtooth sides, acupuncture type needles, etc.

The length of the piercing and cutting means is preferably about several 100 micrometers to several millimeters, but is not particularly limited. Further, regarding the disposition and construction of the same, the means may be disposed at the center of the suction portion or the periphery of the same. It is sufficient if the means can make use of the stretching action of the epidermis by the vacuum suction to painlessly and effectively pierce or cut through the epidermis.

EXAMPLES

The present invention will now be further illustrated by, but is by no means limited to, the following Examples.

Figure 1:
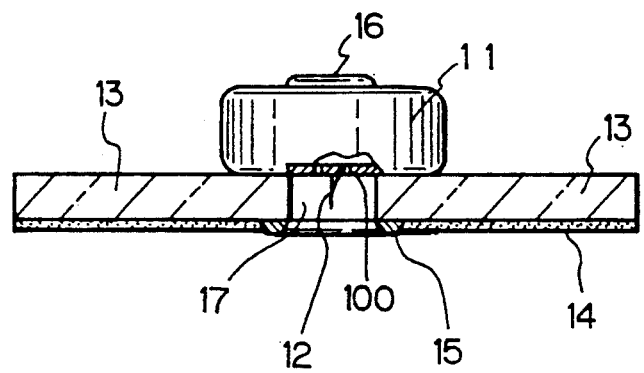
FIG. 1 is a view showing an example of the present device.

FIG. 1 is a view showing one example of the present device.

Reference numeral (11) is a vacuum chamber, which houses a vacuum drive portion. At the top of the vacuum chamber (11) is provided a switch (16). By pressing this switch (16), the vacuum operation is performed. Reference numeral (100) is a hole portion, one or more of which are provided through the bottom of the vacuum chamber.

Reference numeral (12) is a piercing means, which is formed by, for example, a fine needle and is provided at the bottom of the vacuum chamber (11) near the hole portions (100). Reference numeral (13) is a support member, which is formed as a concentric cylindrical film by plastic, rubber, paper, or another material having flexibility. The vacuum chamber (11) is joined to the support member (13) on the top of the same at the periphery near the approximate center of the concentric portion. Reference numeral (14) is an adhesive. Use is made of a material which does not react with the body, such as a material used for adhesive plaster. The adhesive (14) is provided at the bottom of the support member (13) at the outer periphery of the same. Examples of such an adhesive are rubber-based adhesives, acryl-based adhesives, silicone-based adhesives.

Reference numeral (15) is a stopper, which keeps down the elongation and contraction of the support member (13) at the time of application of vacuum and assists the skin in being pulled up. The stopper (15) is provided at the bottom of the periphery of the approximate center of the concentric portion of the bottom of the support member (13). The material for the stopper is desirably rubber, plastic, etc. so as to cause large friction with the skin. Reference numeral (17) is a suction portion, which portion is formed to cover the inside surface of the concentric portion of the support member (13) and the bottom portion of the vacuum chamber, including the piercing means (12) and the hole portions (100).

Figure 2:
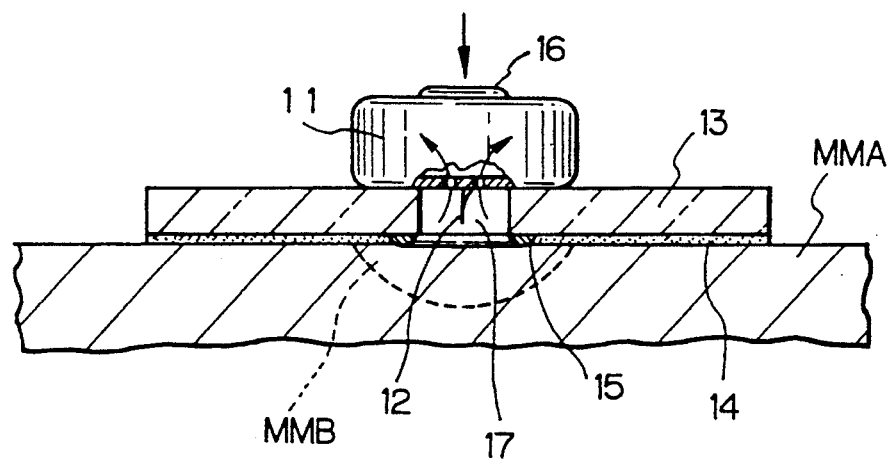
FIGS. 2 and 3 are views for explaining the operation of the example shown in FIG. 1.

Next, the operation of the example shown in FIG. 1 mentioned above will be explained in detail with reference to FIG. 2 and FIG. 3.

First, the above-mentioned example of the present invention is placed, with the adhesive portion (14) down, on a position of the subject's skin (MMA) suitable for sampling blood. The adhesive portion (14) adheres to the subject's skin (MMA), so the device is affixed to the surface of the subject's skin and the suction portion (17) is sealed. At this time, the piercing means does not contact the subject's skin.

The switch (16) is depressed. The vacuum chamber thereby begins the vacuum operation. By this vacuum operation, the suction portion (17) enters a vacuum state through the holes (100) and a suction action is applied to the subject's skin under the suction portion (17).

By this suction action, the body fluid, including the blood, inside the subject's skin (MMA) begins to engorge, forming the engorged position (MMB).

Figure 3:
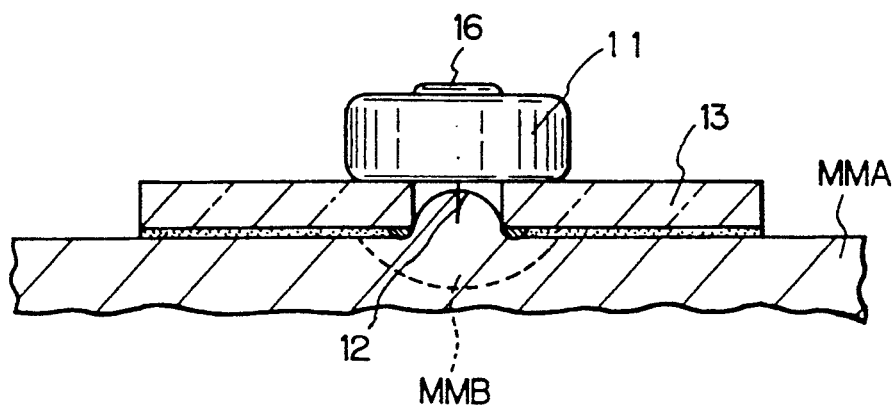

Gradually, as shown in FIG. 3, the subject's skin under the suction portion (17) begins to rise up and contacts the piercing means (12). The subject's skin at this portion, in the pulled up state, is locally taut, so the piercing means (12) easily pierces the epidermis at the subject's skin (MMA) and the vacuum reaches the engorged portion (MMB). At this time, the stopper (15) prevents the movement of the skin under the stopper (15) by a suction action and assists the surface of the subject's skin being raised up. The blood and other body fluid travel along the piercing means (12) and are sucked out to the surface of the subject's skin where they are collected. In accordance with need, further, the blood sucked out to the surface of the subject's skin is taken into the inside of the vacuum chamber (11) through the holes (100).

Finally, the device of this example is taken off the subject's skin surface (MMA).

Figure 4:
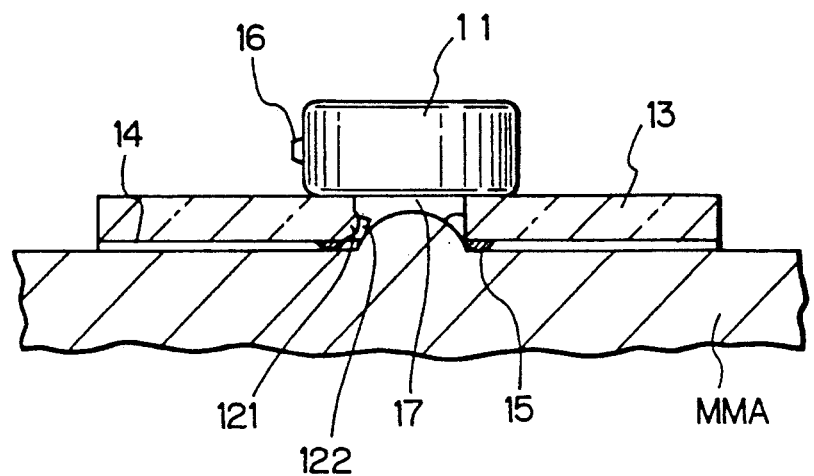
FIG. 4 is a sectional view showing another example of the present device.
Figure 5:
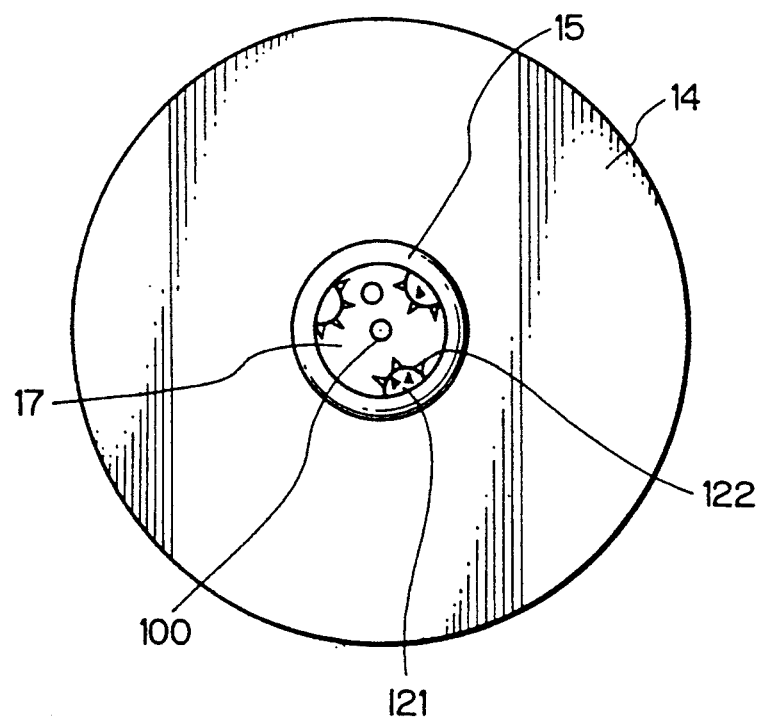
FIG. 5 is a bottom view of the example shown in FIG. 4.

Further, FIG. 4 shows a cutting means (121) disposed at the periphery of the suction portion. When the epidermis is pulled up and stretched by the vacuum, the surface of the epidermis contacts and slides against the fine sawtooth edge (122) of the cutting means and is painlessly cut. The cutting means is formed to have a sawtooth edge construction over all or part of its edge. FIG. 5 is a view looking at FIG. 4 from the bottom. Reference numeral (100) is a hole portion, which communicates the vacuum chamber (11) with the suction portion (17). The rest of the construction is the same as in FIG. 1, so the same reference numerals are attached and the explanations are omitted.

Figure 6:
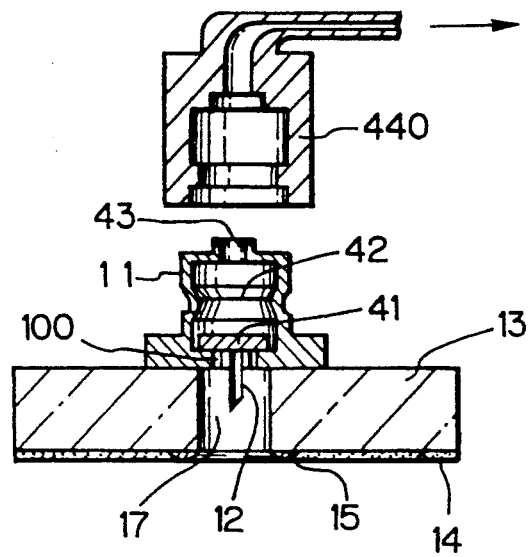
FIG. 6 is a sectional view showing another example of the present device.

Next, another example will be shown in FIG. 6. In FIG. 6, a vacuum drive portion (not shown) is provided outside and the piercing means is made a hollow needle.

Reference numeral (11) is a vacuum chamber in the same way as in FIG. 1 and has a cylindrical shape. Reference numeral (41) is a valve, which moves up and down in the cylindrical vacuum chamber. Reference numeral (42) is a friction portion, which is formed at the bottom of the cylindrically shaped inside of the vacuum chamber (11). Reference numeral (43) is an opening, which serves as an interface between the inside of the vacuum chamber and the outside vacuum drive means. The interface of the outside vacuum drive means is shown by reference numeral (440).

Reference numeral (12) is a piercing means, which is formed by a hollow needle. The hollow needle reaches into the inside of the vacuum chamber. Reference numeral (100) is a hole portion, which connects the inside of the vacuum chamber and the suction portion (17). The rest of the construction is the same as in the example of FIG. 1 and will therefore not be explained.

Next, the operation of the example shown in FIG. 6 will be explained.

The device according to this example is placed on the surface of the body. The adhesive portion (14) is joined to the surface of the body. The interface (440) of the outside vacuum drive means is connected to the top of the vacuum chamber. The outside vacuum drive means is driven. The valve (41) begins to move upward. Since the valve (41) contacts the friction portion (42), it gradually moves upward. When the valve begins to move upward, the gas in the suction portion (17) moves upward through the hole portion (100). At the same time, the subject's skin under the suction portion (17) rises up and engorges with blood.

Along with the valve (41) moving upward, the skin under the suction portion (17) rises up. When it passes the friction portion (42), the valve (42) moves up all at once and the skin under the suction portion (17) rises up to the maximum extent possible, contacts the piercing member (12), and is pierced.

When pierced, the piercing means (12) reaches the engorged portion under the skin. The blood is taken into the vacuum chamber (11) through the piercing means (12). After the blood is collected, the interface (440) is removed. The valve (41) falls, but stops at the top of the friction portion (42), preventing leakage of the collected blood from the hole portion (100).

Figure 7:
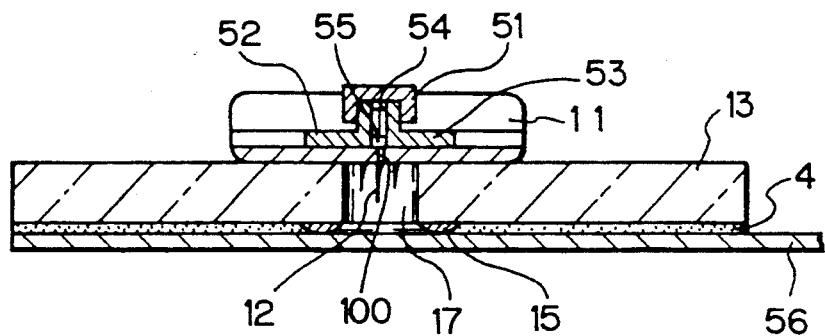
FIG. 7 is a sectional view showing another example of the present device.

Next, a further example will be shown in FIG. 7 and explained.

The device according to this example shown in FIG. 7 is provided with a vacuum drive portion inside and further has a plurality of piercing means.

Reference numeral (51) is a holding piece which is provided so that a sliding member A (52) and a sliding member (B) are held at predetermined positions so as not to separate.

The sliding member A (52) and the sliding member B (53) slide left and right and are connected by a spring (54). The portion over which the sliding member A (52) and the sliding member B (53) face each other constitutes a vacuum space (55).

Reference numeral (12) is a needle, a plurality of which are provided at the bottom of the vacuum chamber (11). Reference numeral (100) is a hole portion, of which a plurality are made and which connect the vacuum space (55) and the suction portion (17). Reference numeral (56) is a peeling member, which prevents the drying and reduction of tackiness of the adhesive (14) and which is peeled off at the time of use.

The rest of the construction is the same as in the example shown in FIG. 1 and thus will not be explained.

Figure 8:
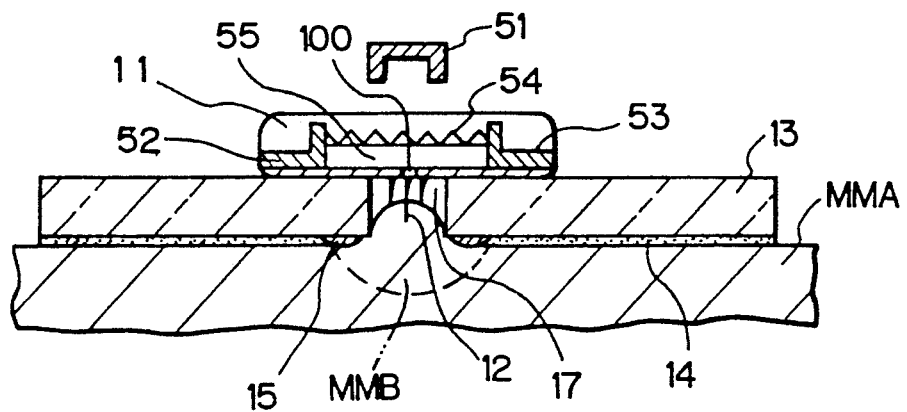
FIG. 8 is a view for explaining the operation of the example shown in FIG. 7.

Next, an explanation will be made of the operation of the example shown in FIG. 7, including FIG. 8.

At the time of use, the peeling member (56) is peeled off and the device is placed on the position of the body for drawing the blood. The sliding member A (52) and the sliding member B (53) are affixed at predetermined positions by a holding piece (51). At this time, a spring (54) maintains the compressed state.

Next, the holding piece (51) is removed, as shown in FIG. 6. The sliding member A (52) and the sliding member B (53) are pushed outward by the force of the release of the spring (54) and the vacuum space (55) grows in volume. At the time of adhesion, the suction portion (17) and the vacuum space (55) were sealed by the subject's skin, so when the vacuum space (55) grows, the skin under the suction portion (17) is pulled up.

Blood engorges under the skin and the surface rises up. The piercing means (12) contacts the skin, then pierces through it. When the piercing means (12) reaches the engorged portion, the blood comes out along the surface of the piercing means (12) and is thus extracted.

The time waiting for blood to engorge after the skin is drawn up and the time until the piercing means pierces the skin also may be suitably selected. Further, it is not that particularly necessary to wait for the blood to engorge. So long as the skin is pierced by the piercing means in a state after suction when there is tautness in the skin due to its being drawn up, the present device operates sufficiently.

Figure 9:
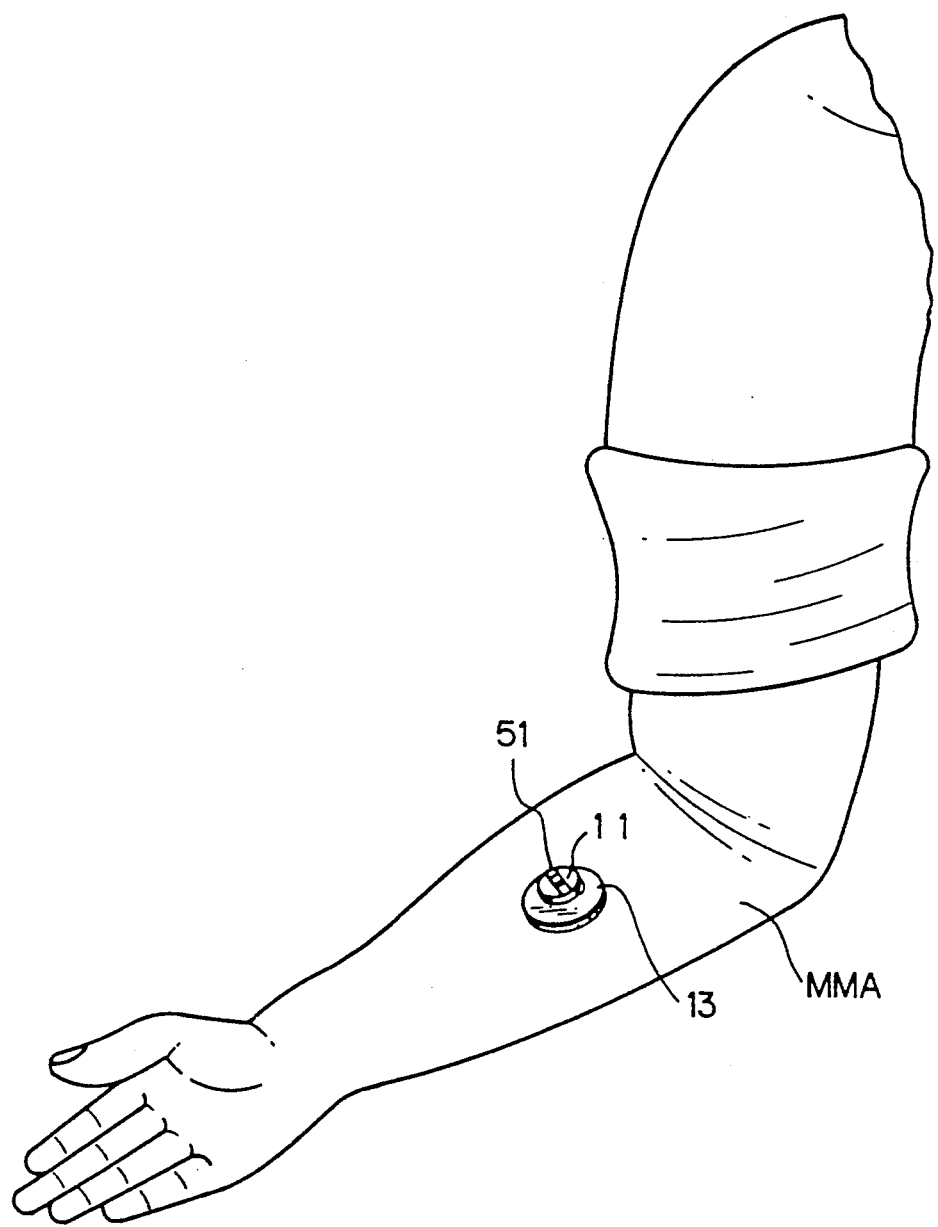
FIG. 9 is a view for explaining the case of use of the example shown in FIG. 7.

Next, the state of one of the examples shown in FIG. 7 adhered to the upper arm of the body is shown in FIG. 9. Reference numeral (11) shows a vacuum chamber, and (13) a support member. Since the device is small in size and light in weight, it may be used adhered in the manner shown in FIG. 9 as well. Also, the adhesive portion is suitably used. It is also possible to use the device with no adhesive portion, i.e., held by the hand.

As explained above in detail, the present device is small in size, light in weight, and low in price and therefore has the effects that it is suited as a disposable implement and further enables blood to be drawn reliably etc.

I claim:

1. A skin-adhesive blood sampling device comprising:
    a sealed vacuum chamber in a state of preexisting reduced pressure;
    a support member for the sealed vacuum chamber, said support member defining a suction portion adjacent the sealed vacuum chamber, said suction portion, in cooperation with said sealed vacuum chamber, exposing an area of skin of a patient to a reduced pressure state when the device is actuated;
    means arranged within the suction portion for slightly rupturing a portion of the area of skin of the patient exposed to the reduced pressure state; and
    said support member having adhesive means for securely fixing the device to a surface of the body of the patient so as to maintain the reduced pressure state during suction and collection of blood through the slightly ruptured portion of the area of skin of the patient.

2. The device as claimed in claim 1 wherein the support member further comprises a stopper material arranged around an outer periphery of the suction portion so as to cause friction with skin thereunder.

3. The device as claimed in claim 1 wherein the rupturing means is disposed along an inner periphery of the suction portion so as to painlessly cut epidermis sliding thereto.

4. The device as claimed in claim 2 wherein the rupturing means is disposed along an inner periphery of the suction portion so as to painlessly cut epidermis sliding thereto.

5. The device as claimed in claim 1 wherein the rupturing means is a cutting means.

6. The device as claimed in claim 1 wherein the rupturing means is a piercing means.

* * * * *